United States Patent
Engels et al.

(10) Patent No.: US 11,638,729 B2
(45) Date of Patent: May 2, 2023

(54) SYNBIOTIC COMPOSITION FOR PREVENTING DISORDERS

(71) Applicant: N.V. NUTRICIA, Zoetermeer (NL)

(72) Inventors: Eefje Engels, Utrecht (NL); Cornelus Johannes Petrus Van Limpt, Utrecht (NL); Annemarie Oosting, Utrecht (NL); Akhtar Raish Oozeer, Utrecht (NL); Jan Knol, Utrecht (NL); Mona Mischke, Utrecht (NL)

(73) Assignee: N.V. Nutricia, Zoetermeer (NL)

(*) Notice: Subject to any disclaimer, the term of this patent is extended or adjusted under 35 U.S.C. 154(b) by 0 days.

(21) Appl. No.: 16/730,538

(22) Filed: Dec. 30, 2019

(65) Prior Publication Data

US 2020/0147154 A1 May 14, 2020

Related U.S. Application Data

(63) Continuation of application No. PCT/EP2018/067703, filed on Jun. 29, 2018.

(30) Foreign Application Priority Data

Jun. 30, 2017 (EP) .................................... 17179070

(51) Int. Cl.

| | | |
|---|---|---|
| A61K 35/745 | (2015.01) | |
| A61K 31/702 | (2006.01) | |
| A23L 33/21 | (2016.01) | |
| A23L 33/135 | (2016.01) | |
| A23L 33/00 | (2016.01) | |
| A61K 31/202 | (2006.01) | |
| A61K 31/715 | (2006.01) | |

(52) U.S. Cl.
CPC .......... A61K 35/745 (2013.01); A23L 33/135 (2016.08); A23L 33/21 (2016.08); A23L 33/40 (2016.08); A61K 31/202 (2013.01); A61K 31/702 (2013.01); A61K 31/715 (2013.01)

(58) Field of Classification Search
CPC ... A61K 35/745; A61K 31/702; A23L 33/135; A23L 33/40
See application file for complete search history.

(56) References Cited

U.S. PATENT DOCUMENTS

| | | | |
|---|---|---|---|
| 9,314,047 B2* | 4/2016 | Speelmans | A61P 37/02 |
| 9,386,793 B2 | 7/2016 | Blaser et al. | |
| 9,456,629 B2* | 10/2016 | Hougee | A61K 31/702 |
| 9,480,670 B2 | 11/2016 | Mace et al. | |
| 2012/0171167 A1* | 7/2012 | Kondo | A61P 3/04 |
| | | | 424/93.4 |

FOREIGN PATENT DOCUMENTS

| | | |
|---|---|---|
| EP | 2 143 341 A1 | 1/2010 |
| EP | 2 359 838 A1 | 8/2011 |
| EP | 2 452 571 A1 | 5/2012 |
| WO | WO-99/49877 A2 | 10/1999 |
| WO | WO-2006/091103 A2 | 8/2006 |
| WO | WO-2007/073194 A2 | 6/2007 |
| WO | WO-2008/116700 A1 | 10/2008 |
| WO | WO-2011/096808 A1 | 8/2011 |
| WO | WO-2012/153179 A1 | 11/2012 |
| WO | WO-2013/036102 A1 | 3/2013 |
| WO | WO-2013/054002 A1 | 4/2013 |
| WO | WO-2015/172191 A1 | 11/2015 |
| WO | WO-2016/020495 A1 | 2/2016 |
| WO | WO-2016/026684 A1 | 2/2016 |
| WO | WO-2017/043963 A1 | 3/2017 |
| WO | WO-2017/129649 A1 | 8/2017 |
| WO | WO-2017/145415 A1 | 8/2017 |

OTHER PUBLICATIONS

Beutler B. Gene in fat plays key role in insulin resistance. UT Southwestern Medical Center Newsroom. 2020;1-3.*
Swinburn et al. Dissecting Obesogenic Environments: The Development and Application of a Framework for Identifying and Prioritizing Environmental Interventions for Obesity. Preventive Medicine. 1999;29:563-570.*
Reuters. Overweight moms-to-be more likely to have obese kids. New York Post. 2016;1-7.*
Marcovecchio et al. Obesity and Insulin Resistance in Children. JPGN. 2010;51(3):S149-150.*
Asemi, et al.; "Effect of multispecies probiotic supplements on metabolic profiles, hs-CRP, and oxidative stress in patients with type 2 diabetes"; Annals of Nutrition and Metabolism, vol. 63, No. 1-2, pp. 1-9; (2013).
Cani, et al.; "Selective increases of bifidobacterial in gut microflora improve high-fat-diet-induced diabetes in mice through a mechanism associated with endotoxaemia"; Diabetologia, vol. 50, pp. 2374-2383; (2007).
Eslamparast, et al.; "Effects of synbiotic supplementation on insulin resistance in subjects with the metabolic syndrome: a randomised, double-blind, placebo-controlled pilot study"; British Journal of Nutrition; vol. 112, pp. 438-445; (2014).
Grill, et al.; "Effects of Lactobacillus amylovorus and Bifidobacterium breve on cholesterol"; Letters in Applied Microbiology, vol. 31, pp. 154-156; (2000).
International Preliminary Report on Patentability issued in International Application No. PCT/EP2018/067703, dated Sep. 24, 2019.
International Preliminary Report on Patentability issued in International Application No. PCT/EP2018/067706, dated Jun. 21, 2019.
International Preliminary Report on Patentability issued in International Application No. PCT/EP2018/067712, dated Jun. 21, 2019.
International Search Report and Written Opinion issued in International Application No. PCT/EP2018/067703, dated Nov. 16, 2018.

(Continued)

*Primary Examiner* — Lynn Y Fan

(74) *Attorney, Agent, or Firm* — N.V. Nederlandsch Ostrooibureau

(57) ABSTRACT

The invention relates to prevention of insulin resistance or low-grade chronic inflammation later in life upon ingestion of synbiotics early in life.

6 Claims, 2 Drawing Sheets

(56) References Cited

OTHER PUBLICATIONS

International Search Report and Written Opinion issued in International Application No. PCT/EP2018/067706, dated Sep. 24, 2018.
International Search Report and Written Opinion issued in International Application No. PCT/EP2018/067712, dated Sep. 24, 2018.
Kondo, et al.; "Antiobesity Effects of Bifidobacterium breve Strain B-3 Supplementation in a Mouse Model with High-Fat Diet-Induced Obesity"; Biosci Biotechnol Biochem, vol. 74, No. 8, pp. 1656-1661; (2010).
Kuitunen, et al.; "Probiotics prevent IgE-associated allergy until age 5 years in cesarean-delivered children but not in the total cohort"; The Journal of Allergy and Clinical Immunology, vol. 123, No. 2, pp. 335-341; Feb. 2009.
Malaguarnera, et al.; "Bifidobacterium tongum with Fructo-Oligosaccharides in Patients with Non Alcoholic Steatohepatitis"; Digestive Diseases and Sciences, vol. 57, pp. 545-553; (2012).
Melanie, et al.; "Fermented inulin hydrolysate by Bifidobacterium breve as cholesterol binder in functional food application"; Conference Papers: International Symposium on Applied Chemistry (ISAC) 2016.
Mischke, et al.; "Specific synbiotics in early life protect against diet-induced obesity in adult mice"; Diabetes, Obesity and Metabolism, vol. 20, pp. 1408-1418; (2018).
Mofidi, et al.; "Synbiotic supplementation in lean patients with non-alcoholic fatty liver disease: a pilot, randomised, double-blind, placebo-controlled, clinical trial"; British Journal of Nutrition, vol. 117, No. 5, pp. 662-668; (2017).
Moroti, et al.; "Effect of the consumption of a new symbiotic shake on glycemia and cholesterol levels in elderly people with type 2 diabetes mellitus"; Lipids in Health and Disease, vol. 11, No. 29, pp. 1-8; (2012).
Ooi, et al.; "Cholesterol-Lowering Effects of Probiotics and Prebiotics: A Review of in Vivo and in Vitro Findings"; International Journal of Molecular Sciences, vol. 11, Issue 6, pp. 2499-2522; (2010).
U.S. Appl. No. 16/730,525, filed Dec. 30, 2019.
U.S. Appl. No. 16/730,530, filed Dec. 30, 2019.

\* cited by examiner

SYNBIOTIC COMPOSITION FOR PREVENTING DISORDERS

CROSS-REFERENCE TO RELATED APPLICATIONS

The present application is a Continuation of International Patent Application No. PCT/EP2018/067703, filed Jun. 29, 2018, and claims the benefit of priority to European Patent Application No. 17179070.2, filed Jun. 30, 2017, the entire contents of which are hereby incorporated by reference.

FIELD OF THE INVENTION

The present invention is in the field of nutritional compositions for infants and aims at preventing disorders later in life.

BACKGROUND OF THE INVENTION

Breast-feeding is the preferred method of feeding infants. It has been suggested that breast feeding early in life might influence the occurrence of disorders later in life. However, there are circumstances that make breast-feeding impossible or less desirable. In those cases infant formula and follow-on formula are a good alternative. The composition of modern infant or follow-on formulas is already highly adapted in such a way that it meets many of the special nutritional requirements of the fast growing and developing infant.

Still improvements can be made towards the constitution of infant milk formulae. Compared to breast fed infants formula fed infants have an increased risk of becoming obese, developing metabolic health diseases later in life, becoming insulin resistant or acquiring diabetes type 2. Early in life feeding has a lasting programming effect on such disease risks in adulthood. These conditions are major health problems in the Western world and a leading preventable cause of death worldwide, with increasing prevalence in adults and children, and authorities view it as one of the most serious public health problems of the $21^{st}$ century. According to the WHO the number of people with diabetes has risen from 108 million in 1980 to 422 million in 2014, the global prevalence of diabetes among adults over 18 years of age has risen from 4.7% in 1980 to 8.5% in 2014, in 2012, and WHO projects that diabetes will be the 7th leading cause of death in 2030. Previously, type 2 diabetes was predominantly a disease of middle-aged and older people, but nowadays the age of onset has decreased and type 2 diabetes has been reported in adolescents and children worldwide WO 2006/091103 describes a composition comprising *Bifidobacterium* and two non-digestible oligosaccharides to stimulate the intestinal flora of a human milk-fed infant.

WO 2007/073194 describes a composition comprising a lipid component, comprising linoleic acid and alpha-linoleic acid, as well as a protein and a digestible carbohydrate component to prevent obesity later in life.

WO 2011/096808 describes a composition comprising sialyl-oligosaccharide and living *Bacteroides* ssp. to reduce the risk of overweight or obesity of an infant in later life.

U.S. Pat. No. 9,480,670 discloses a nutritional composition comprising a significant amount of arachidonic acid (ARA) is described, as being particularly suitable for infants below the age of 3 years, and for use to reduce the risk of developing overweight/obesity and/or insulin resistance later in life.

SUMMARY OF THE INVENTION

The inventors surprisingly found, when employing animal models, that dietary supplementation with *Bifidobacterium breve* in combination with non-digestible oligosaccharides early in life resulted in later-in-life benefits. In particular it was found that later-in-life, after exposure to a Western Style Diet increased in calories and fat, the glucose homeostasis, was improved resulting in reduced insulin levels, improved insulin sensitivity and reduced low-grade chronic inflammation when compared to the control group that had not received this dietary intervention and was challenged with the Western Style Diet.

The inventors have found in a mouse model that it was possible to program the infants in such a manner that they could better withstand risks commonly associated with a Western Style Diet. When the infants received a diet supplemented with *Bifidobacterium breve* in combination with non-digestible oligosaccharides during their early life, it was found that insulin levels and the index calculated with the Homeostasis Model of Assessment-Insulin Resistance (HOMA-IR) was lower, and the amount of plasma pro-inflammatory cytokines was lower and more comparable to a healthy reference group not exposed to a Western Style Diet. Surprisingly the effects were not, or to a much lesser extent, observed in group that received only non-digestible oligosaccharides without *B. breve*. Therefore the use of *B. breve* together with non-digestible oligosaccharides administered during infancy is particularly suitable to improve hyperinsulinemia, insulin resistance, diabetes type 2 and/or low-grade chronic inflammation later.

DETAILED DESCRIPTION OF THE INVENTION

Thus the present invention concerns a method for preventing and/or reducing the risk of occurrence of hyperinsulinemia, insulin resistance, diabetes type 2 and/or low-grade chronic inflammation later in life in a human subject by administering a nutritional composition comprising a combination of *Bifidobacterium breve* and non-digestible oligosaccharides.

In one embodiment, the present method is a non-medical method for preventing and/or reducing the risk of occurrence of hyperinsulinemia, insulin resistance, diabetes type 2 and/or low-grade chronic inflammation later in life in a human subject by administering a nutritional composition comprising a combination of *Bifidobacterium breve* and non-digestible oligosaccharides.

The invention can also be worded as the use of a combination of *Bifidobacterium breve* and non-digestible oligosaccharides for the manufacture of a nutritional composition for use in preventing and/or reducing the risk of occurrence of hyperinsulinemia, insulin resistance, diabetes type 2 and/or low-grade chronic inflammation later in life in a human subject by administration of the nutritional composition to the human subject early in life.

The invention can also be worded as a nutritional composition comprising a combination of *Bifidobacterium breve* and non-digestible oligosaccharides for use in preventing and/or reducing the risk of occurrence of hyperinsulinemia, insulin resistance, diabetes type 2 and/or low-grade chronic inflammation later in life in a human subject by administration of the nutritional composition to the human subject early in life.

*Bifidobacterium breve*

The nutritional composition in the method or use according to the present invention, hereafter also referred to as the present (nutritional) composition, comprises *Bifidobacterium* breve. It was found that the presence of *B. breve* together with non-digestible oligosaccharides beneficially affects insulin sensitivity and inflammatory status later in life. *Bifidobacterium breve* is a Gram-positive, anaerobic, branched rod-shaped bacterium. The *B. breve* preferably has at least 95% identity with the 16 S rRNA sequence of the type strain of *B. breve* ATCC 15700, more preferably at least 97% identity (Stackebrandt & Goebel, 1994, *Int. J. Syst. Bacteriol.* 44:846-849). Preferred *B. breve* strains are those isolated from the faeces of healthy human milk-fed infants. Typically, these are commercially available from producers of lactic acid bacteria, but they can also be directly isolated from faeces, identified, characterised and produced. According to a preferred embodiment, the present composition comprises at least one *B. breve* selected from the group consisting of *B. breve* Bb-03 (Rhodia/Danisco), *B. breve* M-16V (Morinaga), *B. breve* R0070 (Institute Rosell, Lallemand), *B. breve* BR03 (Probiotical), *B. breve* BR92) (Cell Biotech), DSM 20091, LMG 11613, YIT4065, FERM BP-6223 and CNCM I-2219. Most preferably, the *B. breve* is selected from the group consisting of *B. breve* M-16V and *B. breve* CNCM I-2219, most preferably the *B. breve* is a M-16V. *B. breve* I-2219 was published a.o. in WO 2004/093899 and in U.S. Pat. No. 7,410,653 and was deposited at the Collection Nationale de Cultures de Microorganisms, Institute Pasteur, Paris, France on 31 May 1999 by Compagnie Gervais Danone. *B. breve* M-16V was deposited as BCCM/LMG23729 and is commercially available from Morinaga Milk Industry Co., Ltd.

The present composition preferably comprises viable *B. breve*. The present composition preferably comprises $10^4$ to $10^{12}$ colony forming units (cfu) *B. breve* per gram dry weight of the present nutritional composition, preferably $10^4$ to $10^{11}$, more preferably $10^5$ to $10^{10}$, most preferably from $10^6$ to $1\times10^9$ cfu *B. breve* per gram dry weight of the present composition. Preferably the composition comprises $10^4$ to $10^{13}$ cfu *B. breve* per 100 ml, more preferably $10^6$ to $10^{11}$ cfu *B. breve* per 100 ml, most preferably $10^7$ to $10^{10}$ cfu *B. breve* per 100 ml. In the context of the present invention, it is to be understood that the nutritional composition preferably does not comprise other probiotic bacteria, hence probiotic bacteria other than *Bifidobacterium breve* preferably are excluded from the nutritional composition in the method or use according to the present invention.

Non-Digestible Oligosaccharides

The nutritional composition in the method or use according to the present invention comprises non-digestible oligosaccharides (NDO). The term "oligosaccharide" as used in the present invention preferably refers to a saccharide with a degree of polymerization (DP) of 2 to 250, preferably a DP of 2 to 100, more preferably of 2 to 60. It is understood that in the context of this invention a saccharide with a DP in a certain range may include a mixture of saccharides with different average DP's, for example, if an oligosaccharide with a DP of 2 to 100 is included in the present composition, this may include compositions that comprise oligosaccharides with an average DP between 2 and 5, an average DP between 50 and 70 and an average DP between 7 and 60. The term "non-digestible oligosaccharide" as used in the present invention refers to oligosaccharides which are not or only partially digested in the intestine by the action of acids or digestive enzymes present in the human upper digestive tract (small intestine and stomach) but which are fermented by the human intestinal flora. For example, sucrose, lactose, maltose and maltodextrins are considered digestible. For example, galacto-oligosaccharides, fructo-oligosaccharides are considered non-digestible oligosaccharide.

Preferably the non-digestible oligosaccharides are soluble. The term "soluble" as used herein, when having reference to an oligosaccharide, means that the oligosaccharide is soluble according to the method described by L. Prosky et al., J. Assoc. Off. Anal. Chem. 71, 1017-1023 (1988).

The non-digestible oligosaccharide is preferably selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides.

Preferably the present composition comprises fructo-oligosaccharides and/or galacto-oligosaccharides, more preferably galacto-oligosaccharides, most preferably transgalacto-oligosaccharides. In a preferred embodiment the composition comprises a mixture of galacto-oligosaccharides and fructo-oligosaccharides. Preferably the present composition comprises galacto-oligosaccharides with a DP of 2-10, preferably with an average DP between 2 and 10, and/or fructo-oligosaccharides with a DP of 2-60, preferably with an average DP between 2 and 60, preferably with an average DP between 10 and 60, preferably with an average DP between 15 and 60, preferably with an average DP between 20 and 60. The presence of non-digestible oligosaccharides in these preferred embodiments will have an improved effect on preventing or reducing the risk of insulin resistance, diabetes type 2 and/or low-grade chronic infection later in life.

The galacto-oligosaccharide is preferably selected from the group consisting of transgalacto-oligosaccharides. In a particularly preferred embodiment the present method comprises the administration of transgalacto-oligosaccharides ([galactose]$_n$-glucose; wherein n is an integer between 1 and 60, i.e. 2, 3, 4, 5, 6, . . . , 59, 60; preferably n is selected from 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are β-linked.

In one embodiment the nutritional composition in the method or use according to the present invention preferably comprises fructo-oligosaccharide. The term "fructo-oligosaccharide" as used herein refers to a non-digestible polysaccharide comprising a chain of at least 2 β-linked fructose units, with a DP of 2 to 250, preferably 7 to 100, more preferably 20 to 60. In one embodiment preferably insulin is used. Insulin is for example available under the tradename "Raftilin HP®", (Orafti). The average DP of the present fructo-oligosaccharide is preferably at least 7, more preferably at least 10, preferably below 100. The fructo-oligosaccharide used preferably has the (majority of) fructose units linked with a β(2→1) linkage. Other terms for fructooligosaccharides include insulin, fructopolysaccharide, polyfructose, fructans and oligofructose. The present composition preferably comprises fructo-oligosaccharides with a DP of 2 to 200.

In a preferred embodiment, the present composition comprises two or more non-digestible carbohydrates differing in monosaccharide unit composition, or differing in degree of polymerization (DP) or both. Two non-digestible carbohydrates differ in monosaccharide composition when there is at least 30 number % difference, more preferably at least 50 number % difference in monosaccharide composition based on total number of monosaccharide units. For instance galacto-oligosaccharides with an average composition of Glu-Gal3 and fructo-oligosaccharides with an average composition of Glu-Fru3 differ for 75 number %. Two non-digestible carbohydrates differ in DP if the average DP of the two carbohydrates differs more than 5 monosaccharide units, preferably more than 10 units, even more preferably more than 15 units. For example hydrolysed insulin with an average DP of 4 and long chain insulin with an average DP of 25 have a difference in DP of 21 units.

Preferably the present composition comprises galacto-oligosaccharides with an average DP between 2 and 10 and fructo-oligosaccharides with an average DP between 10 and 60. Preferably the present composition comprises fructo-oligosaccharides with an average DP between 2 and 10, and fructo-oligosaccharides with an average DP between 15 and 60. Preferably the present composition comprises galacto-oligosaccharides with an average DP between 2 and 10, and fructo-oligosaccharides with an average DP between 2 and 10. The presence of non-digestible oligosaccharides in these preferred embodiments will have an improved effect on preventing or reducing the risk of insulin resistance, diabetes type 2 and/or low-grade chronic inflammation later in life.

Preferably the present composition comprises galacto-oligosaccharides and fructo-oligosaccharides in a weight ratio of 20 to 0.5, more preferably 20 to 1, most preferably from 12 to 2.

Preferably, the present composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. % non-digestible oligosaccharides.

Preferably the present composition comprises $10^4$ to $10^{12}$ cfu *B. breve* per gram dry weight and 0.25 wt. % to 20 wt. % non-digestible oligosaccharides based on dry weight, more preferably $10^5$ to $10^{10}$ cfu *B. breve* per gram dry weight and 0.5 wt. % to 10 wt. % non-digestible oligosaccharides based on dry weight. Preferably the present composition does not comprise probiotic bacteria other than *Bifidobacterium breve*.

Preferably the present composition comprises $10^4$ to $10^{13}$ cfu *B. breve* and 80 mg to 2 g non-digestible oligosaccharides per 100 ml, more preferably $10^8$ to $10^{11}$ cfu *B. breve* and 300 mg to 1 g non-digestible oligosaccharides per 100 ml. Preferably the present composition does not comprise probiotic bacteria other than *Bifidobacterium breve*.

Preferably the present nutritional composition comprises i) $1×10^5$ cfu to $1×10^{10}$ cfu *B. breve* per gram dry weight, more preferably $1×10^8$ cfu to $1×10^{10}$ cfu; and either ii) 0.5 to 20 wt. % galacto-oligosaccharides based on dry weight, more preferably 0.5 to 10 wt. % galacto-oligosaccharides or iii) 0.05 to 2% fructo-oligosaccharides based on dry weight, more preferably 0.1 to 1 wt. % fructo-oligosaccharides or both ii) and iii). Preferably the present nutritional composition does not comprise probiotic bacteria other than *Bifidobacterium breve*.

Nutritional Composition

The nutritional composition in the method or use according to the present invention is preferably particularly suitable for providing the daily nutritional requirements to a human subject with an age below 36 months, particularly to a human subject with an age below 24 months, even more preferably to a human subject with an age below 18 months, most preferably to an infant below 12 months of age. Hence, the nutritional composition is for feeding or is used for feeding a human subject. The present composition preferably comprises a lipid, and a protein and a digestible carbohydrate component wherein the lipid component preferably provides 30 to 60% of total calories, the protein component preferably provides 5 to 20%, more preferably 5 to 15 wt. %, of the total calories and the digestible carbohydrate component preferably provides 25 to 75% of the total calories. Preferably the present composition comprises a lipid component providing 35 to 50% of the total calories, a protein component provides 6 to 12% of the total calories and a digestible carbohydrate component provides 40 to 60% of the total calories. The amount of total calories is determined by the sum of calories derived from protein, lipids and digestible carbohydrates.

The present composition is not human breast milk. The present composition preferably comprises vegetable lipids. The present composition preferably comprises other fractions, such as vitamins and minerals according to international directives for infant formulae. Preferably the nutritional composition is an infant formula, a follow on formula or a young child formula, more preferably an infant formula or a follow on formula.

Preferably the nutritional composition does not comprise *Lactobacilli*. *Lactobacillus* was found to be reduced in the group that had received *B. breve* and non-digestible oligosaccharides early in life and that had an improved effect on preventing or reducing the risk of insulin resistance, diabetes type 2 and/or low-grade chronic inflammation later in life.

In one embodiment the present composition is a powder suitable for making a liquid composition after reconstitution with an aqueous solution, preferably with water. Preferably the present composition is a powder to be reconstituted with water.

In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably the present composition is in a liquid form, with a viscosity below 35 mPa·s, more preferably below 6 mPa·s as measured in a Brookfield viscometer at 20° C. at a shear rate of 100 $s^{-1}$. Suitably, the composition is in a powdered form, which can be reconstituted with water to form a liquid, or in a liquid concentrate form, which should be diluted with water. When the composition is in a liquid form, the preferred volume administered on a daily basis is in the range of about 80 to 2500 ml, more preferably about 450 to 1000 ml per day.

Use

Employing an animal model it was found that the combination of *B. breve* and non-digestible oligosaccharides, but not non-digestible oligosaccharides alone without *B. breve*, when administered early in life, beneficially affected parameters that are indicative for an improved glucose homeostasis, resulting in improved insulin sensitivity and reduced low-grade chronic inflammation when compared to the control group that had not received this dietary intervention and was challenged with the Western Style Diet.

The present invention relates to a nutritional composition comprising *Bifidobacterium breve* and non-digestible oligosaccharides for use in preventing or reducing the risk of occurrence later in life of hyperinsulinemia, insulin resistance, diabetes type 2 and/or low-grade chronic inflammation, preferably low-grade chronic inflammation later in life.

A significant reduction of insulin levels, gastroinhibitory peptide (GIP), and plasma pro-inflammatory cytokine levels (IL-1α and TNF-α) was observed later in life when the mice were adult and after the mice were subjected to a Western Style Diet was observed. Likewise a reduction of HOMA-IR, amylin and pancreatic polypeptide (PP) and IL-10, IL-15 and IFn-γ was observed. This was observed at post-natal day 98, which is a time point corresponding to adulthood in humans. This indicates that early nutrition has a beneficial effect on hyperinsulinemia, insulin resistance, diabetes type 2 and/or low-grade chronic inflammation extending beyond the period in which it is actually administered. The effects on glucose homeostasis, indicated that the control group that was exposed to a Western Style Diet and had not receive a synbiotic composition early in life leaned towards insulin resistant phenotype, and this was further supported by the effects on the low-grade inflammatory status. Low-grade chronic inflammation is fundamental in inducing insulin resistance and in the progression of insulin resistance to prediabetes to diabetes type 2.

Diabetes is a chronic disease that occurs either when the pancreas does not produce enough insulin or when the body cannot effectively use the insulin it produces. Insulin is a hormone that regulates blood sugar. Hyperglycaemia, or raised blood sugar, is a common effect of uncontrolled diabetes and over time leads to serious damage to many of the body's systems, especially the nerves and blood vessels. Type 2 diabetes (formerly called non-insulin-dependent diabetes or adult-onset diabetes) results from the body's ineffective use of insulin. Until recently, this type of diabetes was seen only in adults but it is now also occurring increasingly frequently in children. Risk factors for diabetes type 2 are associated with insulin resistance. Hyperinsulinemia, or hyperinsulinaemia, is a condition in which there are excess levels of insulin circulating in the blood relative to the level of glucose. Insulin resistance (IR) is a pathological condition in which cells fail to respond normally to the hormone insulin. The body produces insulin when glucose starts to be released into the bloodstream from the digestion of carbohydrates in the diet. Under conditions of insulin resistance, the body produces insulin, but the cells are resistant to the insulin and are unable to use it as effectively, leading to high blood sugar. In turn, beta cells in the pancreas subsequently increase their production of insulin, further contributing to a high blood insulin level. People who develop type 2 diabetes usually pass through earlier stages of insulin resistance and prediabetes.

The homeostasis model assessment-estimated insulin resistance (HOMA-IR) has been widely used for the estimation of insulin resistance in research. Compared with the "gold" standard euglycemic clamp method for quantifying insulin resistance, quantification using HOMA-IR is more convenient. It is calculated multiplying fasting plasma insulin (FPI) by fasting plasma glucose (FPG) given in mmol/l units, then dividing by the constant 22.5, i.e. HOMA-IR= (FPI×FPG)/22.5.

The present composition is to be administered to the human subject early in life. Early in life preferably relates to when the human subject has an age below 36 months, preferably when the human subject has an age below 24 months, even more preferably when the human subject has an age below 18 months, more preferably when the human subject is an infant with an age below 12 months, most preferably when the human subject is an infant with an age below 6 months. In one embodiment, the present composition is administered to a healthy human subject early in life, preferably to a term born human subject.

According to the present invention later in life means preferably when the human subject is a child or preferably an adult. Preferably later in life refers to when the human subject is at an age above 5 years, and more preferably above 18 years. Preventing later in life or reducing the risk of occurrence later in life is different from a direct preventive effect, an effect that occurs when consuming the nutritional intervention, in that it extends its health effect way further in life well after consumption of the nutritional composition has stopped, for example at least 2 years after administration of the formula has stopped, more preferably at least 4 years, more preferably at least 15 years. This later in life effect is believed to be due to a programming effect, wherein early in life, when the human subject is still growing and developing, the organs and its metabolic capacity (such as adipocyte formation, pancreatic B cell mass formation) are programmed during a critical window early in life, and effects happening at this time period have a health effect later in life. Indeed microbiota transfer at postnatal day 42 had no effect on metabolic health indicating that the critical window had passed in the mice.

In a preferred embodiment the nutritional composition comprising *B. breve* and non-digestible oligosaccharides is to be used in a human subject that is exposed to or raised in an obesogenic environment and/or that consumes after infancy a Western Style Diet. A Western Style Diet is increased in fat and is increased in saturated fatty acids, with the fat providing more than 35% of the total calories of the diet, and with the saturated fatty acids providing more than 10% of the total calories of the diet. The term obesogenic environment refers to an environment that promotes gaining weight and to an environment that is not conducive to weight loss within the home or workplace (Swinburn, et al., 1999, Prev Med 29:563-570). In other words, the obesogenic environment refers to an environment that promotes, induces, helps, or contributes to, obesity. Factors that contribute are urbanization, often accompanied by a reduction in physical activity, and easy access to food. In one embodiment the nutritional composition is of particular benefit for infants that are exposed to an environment wherein the average diet is a Western Style Diet that is increased or high in fat and is increased or high in saturated fatty acids, with the fat providing more than 35% of the total calories of the diet, and with the saturated fatty acids providing more than 10% of the total calories of the diet, more in particular a Western Style Diet that is characterised as comprising fat providing between 35 and 45% of the total calories of the diet and comprising saturated fatty acids providing between 10 and 20% of the total calories of the diet.

In a preferred embodiment the human subject is at risk of developing disorders related to an impaired lipid metabolism or impaired liver health, later in life. Therefore the human subject is preferably selected from the group consisting of a preterm infant, a small for gestational age infant, a large for gestational age infant, an infant born form an overweight or obese mother, an infant born from a mother suffering from diabetes type 2 or gestational diabetes, an infant born by C-section and an infant that is being treated or has been treated with antibiotics.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLE 1

Figure 1:
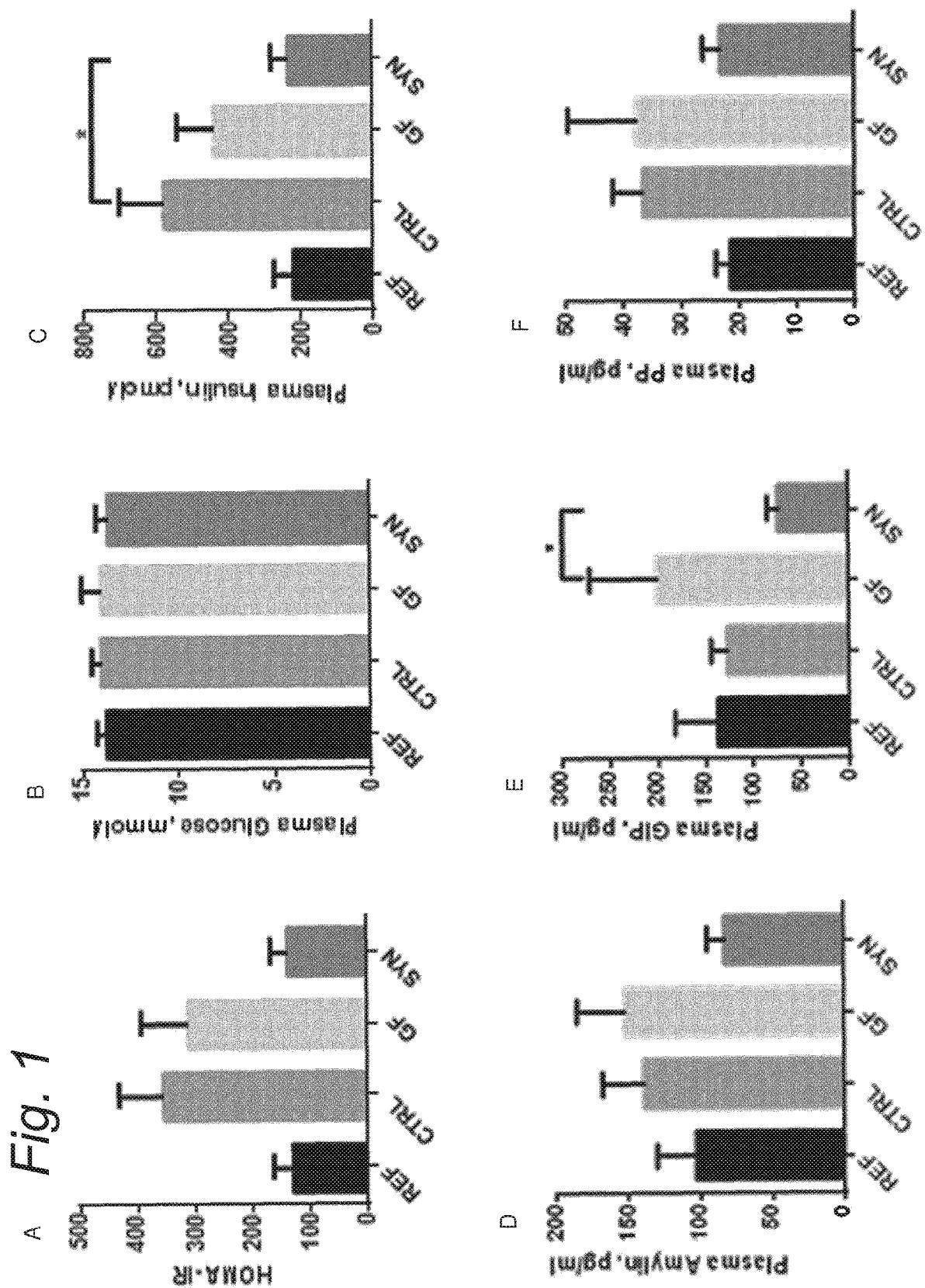
FIGS. 1A-1F show plasma markers for glucose homeostasis at adulthood after early in life nutritional intervention. Data are mean±SEM. *p≤0.05, **p≤0.01. Systemic markers for glucose homeostasis: homeostatic model assessment insulin resistance, HOMA-IR (A), glucose (B), insulin (C), amylin (D), gastric inhibitory polypeptide, GIP (E) and pancreatic polypeptide, PP (F). SYN: group that received $B.$ $breve$ and non-digestible oligosaccharides early in life, followed by a Western Style Diet on day 42-98. G/F: group that received non-digestible oligosaccharides early in life, followed by a Western Style Diet on day 42-98. CTR: group that received no $B.$ $breve$ and no non-digestible oligosaccharides early in life, followed by a Western Style Diet on day 42-98. REF: control group that was raised on standard chow without early in life nutritional intervention or a later in life Western Style Diet challenge.

Later in Life Plasma Signatures Indicative for Glucose Homeostasis are Beneficially Affected by Synbiotics Intervention in Early Life Material & Methods Mice were housed in Macrolon type 2 cages under controlled standard housing conditions and food and water ad libitum. Female and male C57BL/6J mice were obtained from Harlan Laboratories B.V., The Netherlands, and time-mated. On postnatal day (PN)2, litters were culled and four males and two female pups were randomly assigned per dam. During adaptation, pregnancy and lactation, animals were fed an irradiated standard semi-synthetic diet appropriate for breeding according to the recipe of the American Institute of Nutrition (AIN-93G; 16.4 kcal % fat, 18.8 kcal % protein; RDS, The Netherlands). On PN2, lactating dams were assigned to different intervention diets, i.e. different supplementations of the AIN-93G diet, either with non-digestible oligosaccharides [G/F: 2% w/w scGOS (short chain galactooligosaccharides (Vivinal® GOS)):lcFOS (long chain fructo-oligosaccharides (Insulin HP®)) w/w 9:1], synbiotics [SYN: (2% w/w G/F+$10^9$ cfu/g $Bifidobacterium$ $breve$ M-16V (Morinaga Milk Industries Ltd.)] or vehicle control (CTRL: 2% w/w maltodextrin). In addition to the supplementation of the diets, the pups received daily (PN10-15) an oral dose (30 μl) as drops of respective supplement (G/F and maltodextrin approx. 10-15 mg/day, $1\times10^9$ cfu $B.$ $breve$ M-16V). After weaning (PN21), the male offspring was housed in pairs and continued on respective supplemented intervention diet until PN42, a period corresponding with infancy and early childhood in humans. After PN42 until PN98, during adolescence and adulthood, the CTRL, G/F and SYN animals were fed a Western Style Diet (WSD; AIN-93G diet with an adjusted lipid fraction containing 20 wt. % lipid (17 wt. % lard, 3 wt. % soy oil, 0.1 wt. % cholesterol), representing a mild Western Style Diet providing about 40% of the total calories in fat and which contained about 14.5% saturated fatty acids based on total calories) as challenge. This diet has an increased level of fat based on total energy and an increased percentage of saturated fatty acids compared to what is considered healthy.

From PN21 onwards, food intake was determined at continuous intervals by weighing the difference between provided and remaining food. On PN98, after 6 h fasting, the animals were euthanized by isofluran/O2 anesthesia followed by cervical dislocation. Blood samples were collected in $K_3$EDTA-coated microtubes (Greiner Bio-one, Germany). Plasma was obtained from blood samples by centrifugation (1350 g, 10 min, 4° C.) and subsequently snap frozen in liquid nitrogen and stored at −80° C.

In PN98 plasma samples, glucose (GOD-PAP method, Roche diagnostics, Almere, The Netherlands) was measured colorimetrically by using a microplate imaging system (Bio-Rad Laboratories Inc., Hercules, Calif., USA). Fasting plasma insulin, amylin and glucose-dependent insulinotropic polypeptide (GIP) were measured simultaneously using a multiplex approach (MILLIPLEX MAP Mouse Metabolic Hormone Magnetic Bead Panel, Merck KGaA, Darmstadt, Germany). Samples, controls and standards were prepared according to manufacturer's protocol and fluorescence was quantified using a Bio-Plex™ 200 Luminex instrument (Bio-Rad Laboratories Inc., Hercules, Calif., USA). As indirect measure of insulin sensitivity, the homeostasis model assessment of insulin resistance (HOMA-IR; [glu(mmol/l)*ins(pmol/l)/22.5]) was applied for fasting plasma glucose and insulin.

The REF group represent the control group that did not receive the diet intervention (early life phase) and did not receive the WSD challenge diet (later life). In the statistical analyses, the three WSD-challenged groups (CTRL, G/F, SYN) were compared.

Statistical analyses were performed using IBM SPSS Statistics 19.0 (SPSS Benelux, Gorinchem, The Netherlands) and GraphPad Prism 6 (GraphPad Software, La Jolla, Calif., USA). All variables were tested for normal distribution using the One-Sample Kolmogorov-Smirnov Test. If normally distributed, variables were analyzed in CTRL vs. G/F vs. SYN by one-way ANOVA. On significant effects, post hoc analysis using Tukey's multiple comparisons test was performed to compare between the individual groups. In case of non-Gaussian distribution, a log-transformation was performed preceding the one-way ANOVA analysis. Differences were considered significant with p≤0.05. Data are presented as mean±SEM unless otherwise indicated.

Results

Early life nutritional intervention with either G/F or SYN compared to control diet (REF and CTRL group) did not affect developmental growth during and directly after the intervention period until PN42. Body weight, fat mass, and lean body mass did not differ between the experimental groups at this time point. Also fat mass relative to body weight (fat mass %) was similar in all groups. Upon challenge with WSD of CTRL, G/F and SYN groups from PN42 to PN98, animal length, and lean body mass remained similar in all groups, indicating a normal growth trajectory.

Neither in the early life (PN21-42) nor in the later life period (PN42-93), differences in food intake between were detected that could account for observed phenotypes.

FIG. 1 shows the effect of glucose metabolism. HOMA-IR calculation was based on fasted plasma glucose and insulin levels, of which the former was—unsurprisingly—similar in all groups and the latter was significantly different (p=0.039) with CTRL, G/F and SYN showing a stair-like descending pattern, and this indicates a reduced hyperinsulinemia. HOMA-IR was lower in SYN than in CTRL and hence indicated a more sensitive insulin response (or reduced insulin resistance) of the organism. While fasted plasma glucose levels (FIG. 1B) are similar in all groups, the HOMA-IR (FIG. 1A), which is an index for insulin sensitivity, and various signalling molecules relevant for the glucose homeostasis, including insulin (FIG. 1C), amylin (FIG. 1D), GIP (FIG. 1E) and PP (FIG. 1F), show improved (trend-wise) plasma levels in SYN after WSD challenge on PN98, with plasma insulin in SYN being significantly lower than in CTRL. Plasma GIP, a potent incretin that is also known to affect glucose uptake, was similarly high in all groups expect for SYN, which was significantly lower than G/F (p=0.014).

Figure 2:
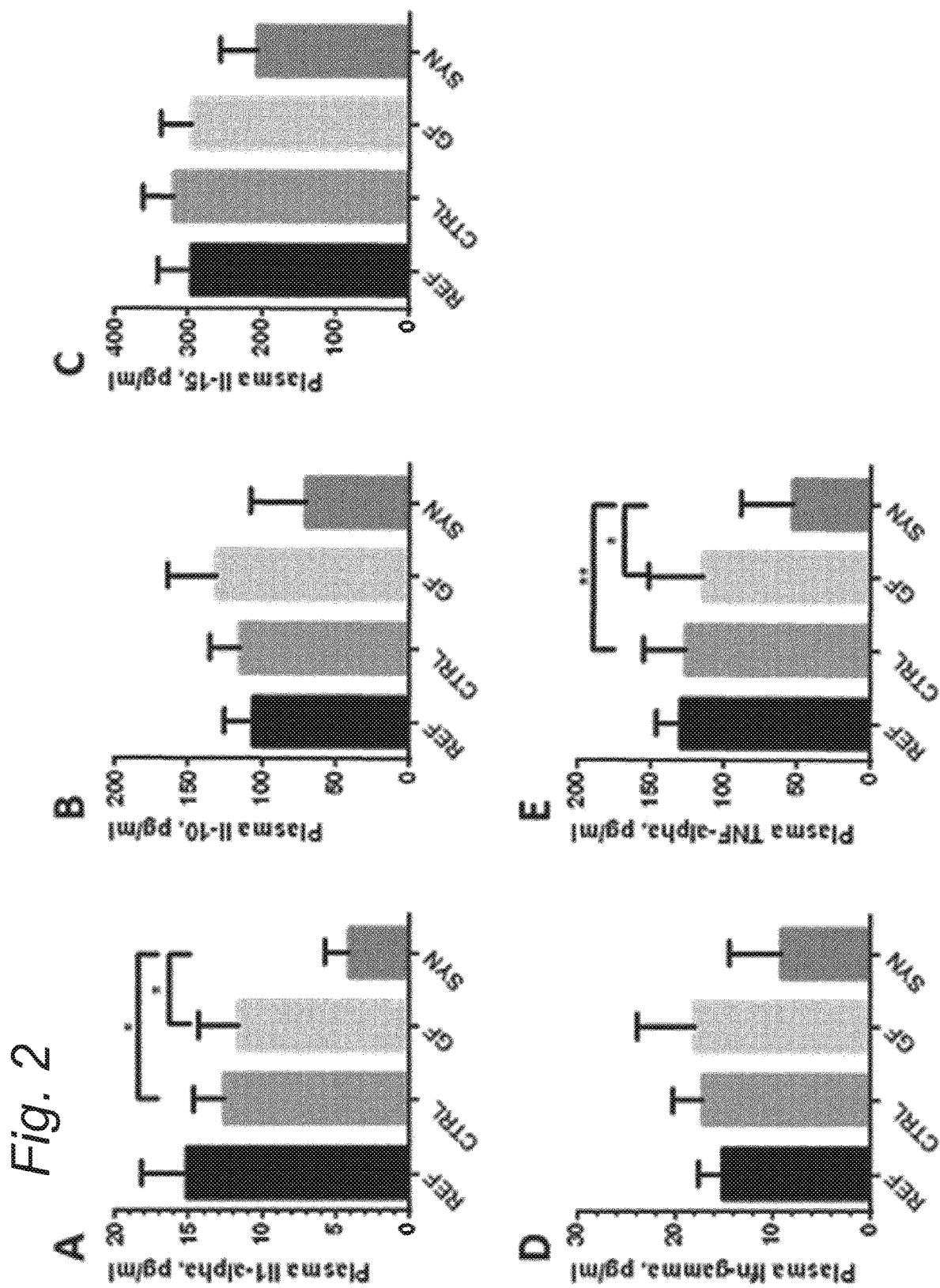
FIGS. 2A-2E show immune markers indicative for chronic inflammation at adulthood after early in life nutritional intervention. Data are mean±SEM. *p≤0.05, **p≤0.01. Systemic markers for inflammation: IL-1α (A), IL-10 (B), IL-15 (C), IFn-γ (D), TNF-α (E) (IL=interleukin; IFn=interferon; TNF=tumor necrosis factor). SYN: group that received $B.$ $breve$ and non-digestible oligosaccharides early in life, followed by a Western Style Diet on day 42-98. G/F: group that received non-digestible oligosaccharides early in life, followed by a Western Style Diet on day 42-98. CTR: group that received no $B.$ $breve$ and no non-digestible oligosaccharides early in life, followed by a Western Style Diet on day 42-98. REF: control group that was raised on standard chow without early in life nutritional intervention or a later in life Western Style Diet challenge.

The low-grade inflammatory status later in life is decreased by synbiotics supplementation in early life, as shown in FIG. 2. A significant decrease of IL-1α (FIG. 2A) and TNF-α (FIG. 2E), as well as trend-wise decrease of IL-10 (FIG. 2B), Il-15 (FIG. 2C) and IFn-γ (FIG. 2D) was seen. Thus early life synbiotics affect the long-term systemic immune status.

The effects on glucose homeostasis, indicate that the CTRL group leans towards an insulin resistance phenotype, and this is further supported by the effects low-grade chronic inflammation. Hence insulin resistance and hyperinsulinemia is prevented/rescued in SYN and the risk to develop diabetes type 2 phenotype is reduced.

EXAMPLE 2

Microbiota Modulation Alone does not Result in Long Term Effect on Metabolic Health Germ-free C57/B16 male mice maintained on autoclaved standard chow were used for transplantation. On week 5, all the mice were acclimatized to sterile WSD for 1 week. Frozen contents from cecum of chow (CTRL) and synbiotic (SYN) supplemented mice (collected at PN42 from feeding experiment) were homogenized in PBS buffer supplemented with reducing solution (0.02M Na2S and 1% cystein dissolved in NaHCO3 buffer). Two separate donors from each group were selected. Following one week of acclimatization, mice (6 weeks old, PN42, 4-5 mice per group) were fasted for 4 h and gavaged with the resultant slurry (200 µl). Transplanted mice were maintained in autoclaved individual ventilated cages with sterile bedding and fed sterile WSD and autoclaved water ad libitum for 14 weeks. Body weight was measured and whole body magnetic resonance imaging (MRI) was performed on PN 42, 43, 70 and 98.

At the time of transfer (PN42), there were no differences in the body weight, fat mass and lean body mass between recipient GF mice. Following microbiota transfer, we observed no significant differences in body weight, fat mass and lean body mass between CTRL and SYN groups for diet*time interaction. Thus, the altered microbiota following synbiotic supplementation is not sufficient to transfer the beneficial phenotype of synbiotic-supplemented mice to recipients. It indicates that it is rather the actual process of early life microbiota modulation by the presence of non-digestible oligosaccharides and *B. breve* early in life in the gut that can be considered necessary to induce a long term metabolic health effect.

The invention claimed is:

1. A method of reducing the risk of occurrence of hyperinsulinemia, insulin resistance and/or diabetes type 2 in a human subject above 5 years of age, comprising administering to the human subject when 0 to 36 months of age a nutritional composition, comprising *Bifidobacterium breve* and a mixture of galacto-oligosaccharides and fructooligosaccharides, wherein the nutritional composition is an infant formula or follow on formula or young child formula, wherein the human subject is at increased risk of developing hyperinsulinemia, insulin resistance and/or diabetes type 2 due to being an infant born from a mother suffering from diabetes type 2 or gestational diabetes and wherein the human subject consumes after infancy a Western Style Diet that is increased in fat and is increased in saturated fatty acids, with the fat providing more than 35% of the total calories of the diet, and with the saturated fatty acids providing more than 10% of the total calories of the diet and wherein administration of the composition decreases plasma glucose-dependent insulinotropic polypeptide (GIP).

2. The method according to claim 1 wherein the composition is administered to the human subject when 0 to 12 months of age.

3. The method according to claim 1, wherein the risk of occurrence of hyperinsulinemia, insulin resistance and/or diabetes type 2 is reduced when the human subject is above 18 years of age.

4. The method according to claim 1, wherein the *Bifidobacterium breve* is *Bifidobacterium breve* M-16V.

5. The method according to claim 1, wherein the nutritional composition is an infant formula or follow on formula.

6. The method according to claim 1, wherein the nutritional composition comprises $10^4$ to $10^{12}$ cfu *Bifidobacterium breve* per gram dry weight of the nutritional composition and 0.25 to 20 wt % of the mixture of galacto-oligosaccharides and fructooligosaccharides based on dry weight of the nutritional composition.

* * * * *